(12) United States Patent
McClanahan

(10) Patent No.: US 6,714,924 B1
(45) Date of Patent: Mar. 30, 2004

(54) COMPUTER-IMPLEMENTED NEURAL NETWORK COLOR MATCHING FORMULATION SYSTEM

(75) Inventor: Craig J. McClanahan, Bowling Green, OH (US)

(73) Assignee: BASF Corporation, Southfield, MI (US)

( * ) Notice: Subject to any disclaimer, the term of this patent is extended or adjusted under 35 U.S.C. 154(b) by 436 days.

(21) Appl. No.: 09/778,819

(22) Filed: Feb. 7, 2001

(51) Int. Cl.[7] .............................. G06E 1/00; G06E 3/00; G06F 15/18; G06N 3/02; G06G 7/00

(52) U.S. Cl. .............................. 706/15; 706/6; 706/31; 706/41; 706/2; 700/48; 700/49; 382/156; 382/162

(58) Field of Search .............................. 706/2, 15, 6, 31, 706/41; 700/48, 49, 50, 51, 30, 31; 382/156, 157, 158, 162, 165

(56) References Cited

U.S. PATENT DOCUMENTS

| | | | |
|---|---|---|---|
| 5,386,496 A | 1/1995 | Arai et al. | 395/22 |
| 5,410,637 A | 4/1995 | Kern et al. | 395/61 |
| 5,424,959 A * | 6/1995 | Reyes et al. | 702/28 |
| 5,546,195 A | 8/1996 | Arai | 358/518 |
| 5,559,173 A * | 9/1996 | Campo et al. | 523/303 |
| 5,559,604 A | 9/1996 | Arai | 356/402 |
| 5,579,031 A | 11/1996 | Liang | 345/154 |
| 5,583,642 A | 12/1996 | Nakazono | |
| 5,673,565 A * | 10/1997 | Jeong et al. | 62/80 |
| 5,680,333 A | 10/1997 | Jansson | 364/578 |
| 5,687,000 A | 11/1997 | Nakaoka | 358/296 |
| 5,729,360 A | 3/1998 | Kita et al. | 358/500 |
| 5,761,070 A | 6/1998 | Conners et al. | 364/478.11 |
| 5,771,311 A | 6/1998 | Arai | 382/162 |

(List continued on next page.)

FOREIGN PATENT DOCUMENTS

| | | | | |
|---|---|---|---|---|
| EP | 484 564 | | 11/1990 | G01J/3/46 |
| EP | 0 822 396 A1 | | 2/1998 | |
| EP | 0 932 038 | | 1/1999 | G01N/21/47 |
| GB | 1056358 | | 10/1963 | |
| WO | WO 94/14039 | | 6/1994 | G01J/3/46 |
| WO | WO 98/12520 | | 3/1998 | G01J/3/46 |
| WO | WO 99/01982 | | 1/1999 | H04N/1/60 |
| WO | WO 00/65847 | | 11/2000 | H04N/9/64 |
| WO | WO 02/063556 A2 | * | 8/2002 | G06N/3/02 |

OTHER PUBLICATIONS

BASF Corporation, et al. International Search Report PCT/US02/14091 International filing date Mar. 5, 2002.

BASF Corporation, et al. International Search Report PCT/US02/14092 International filing date Mar. 5, 2002.

International Search Report for PCT/US 02/00408 filed Aug. 8, 2002.

PCT International Search Report dated Aug. 19, 2003.

*Primary Examiner*—Ramesh Patel (57) ABSTRACT

A method and apparatus for color matching are provided, in which paint recipe neural networks are utilized. The color of a standard is expressed as color values. The neural network includes an input layer having nodes for receiving input data related to paint bases. Weighted connections connect to the nodes of the input layer and have coefficients for weighting the input data. An output layer having nodes are either directly or indirectly connected to the weighted connections and generates output data related to color values. The data to the input layer and the data from the output layer are interrelated through the neural network's nonlinear relationship. The paint color matching neural network can be used for, but not limited to, color formula correction, matching from scratch, effect pigment identification, selection of targets for color tools, searching existing formulas for the closest match, identification of formula mistakes, development of color tolerances and enhancing conversion routines.

40 Claims, 8 Drawing Sheets

U.S. PATENT DOCUMENTS

| | | | |
|---|---|---|---|
| 5,774,230 A | 6/1998 | Goto | 358/298 |
| 5,798,943 A | 8/1998 | Cook et al. | 364/526 |
| 5,808,621 A | 9/1998 | Sundaresan | |
| 5,813,798 A * | 9/1998 | Whiffen | 405/52 |
| 5,864,834 A | 1/1999 | Arai | 706/16 |
| 5,899,605 A | 5/1999 | Caruthers, Jr. et al. | 399/223 |
| 5,907,495 A * | 5/1999 | Snyder et al. | 703/6 |
| 5,929,906 A | 7/1999 | Arai et al. | 348/223 |
| 5,929,998 A | 7/1999 | Kettler et al. | 356/405 |
| 6,081,796 A * | 6/2000 | Takagi et al. | 706/1 |
| 6,088,475 A | 7/2000 | Nagashima et al. | 382/162 |

* cited by examiner

COMPARISON OF THE COLOR MATCHING CAPABILITIES OF THE NEURAL NETWORK & EXTENDED KUBLEKA-MUNK APPROACHES FOR METALLIC & PEARL COLORS

| STANDARDS | | COLOR VALUES | | | CORRECTIONS | | COLOR DIFFERENCES | | | |
|---|---|---|---|---|---|---|---|---|---|---|
| | | L* | a* | b* | | | dE 25 | dE 45 | dE 75 | dE TOTAL |
| BRIGHT SILVER | 25 | 98.75 | -0.95 | -2.14 | START | | 0.99 | 2.52 | 3.27 | 6.78 |
| | 45 | 59.82 | -0.23 | -2.13 | EXTENDED K-M | | 5.06 | 2.47 | 1.74 | 9.26 |
| | 75 | 36.12 | 0.14 | -1.65 | NEURAL NETWORK | | 0.77 | 0.50 | 0.37 | 1.64 |
| | | L* | a* | b* | | | dE 25 | dE 45 | dE 75 | dE TOTAL |
| MEDIUM SILVER | 25 | 74.37 | -0.18 | 4.35 | START | | 2.53 | 4.44 | 6.03 | 13.00 |
| | 45 | 43.85 | -0.08 | 2.92 | EXTENDED K-M | | 4.98 | 1.15 | 0.42 | 6.56 |
| | 75 | 24.91 | 0.15 | 2.98 | NEURAL NETWORK | | 1.10 | 0.81 | 1.06 | 2.97 |
| | | L* | a* | b* | | | dE 25 | dE 45 | dE 75 | dE TOTAL |
| BRIGHT BLUE | 25 | 76.61 | -1.32 | -21.44 | START | | 0.87 | 2.45 | 2.97 | 6.28 |
| | 45 | 42.34 | 0.67 | -15.78 | EXTENDED K-M | | 2.82 | 1.18 | 0.19 | 4.20 |
| | 75 | 22.27 | 2.10 | -11.95 | NEURAL NETWORK | | 0.54 | 0.28 | 0.70 | 1.53 |
| | | L* | a* | b* | | | dE 25 | dE 45 | dE 75 | dE TOTAL |
| LIGHT GREEN | 25 | 85.90 | -5.17 | 8.93 | START | | 1.04 | 2.23 | 3.21 | 6.48 |
| | 45 | 61.00 | -5.29 | 3.93 | EXTENDED K-M | | 1.24 | 0.20 | 0.88 | 2.33 |
| | 75 | 43.08 | -6.01 | 0.29 | NEURAL NETWORK | | 1.03 | 0.76 | 1.09 | 2.88 |
| | | L* | a* | b* | | | dE 25 | dE 45 | dE 75 | dE TOTAL |
| DARK GREEN | 25 | 24.83 | -11.64 | -4.90 | START | | 4.79 | 1.70 | 0.36 | 6.85 |
| | 45 | 8.63 | -4.75 | -4.44 | EXTENDED K-M | | 2.40 | 0.62 | 0.66 | 3.67 |
| | 75 | 3.74 | -0.69 | -2.88 | NEURAL NETWORK | | 1.44 | 0.54 | 0.42 | 2.41 |

NOTES: CIE COLOR VALUES & COLOR DIFFERENCES.

FIGURE 8

NEURAL NETWORK FIT TO A DATABASE
OF 2092 BLUE METALLIC/PEARL COLORS

| dE RANGE * | NUMBER OF COLORS |
|---|---|
| 0 - 1.0 | 20 |
| 1.0 - 2.0 | 450 |
| 2.0 - 3.0 | 755 |
| 3.0 - 4.0 | 537 |
| 4.0 - 5.0 | 226 |
| 5.0 - 6.0 | 72 |
| 6.0 - 7.0 | 14 |
| 7.0 - 8.0 | 12 |
| 8.0 - 9.0 | 4 |
| 9.0 - 10.0 | 1 |
| 10.0 - 11.0 | 1 |

*SUM OF THE COLOR DIFFERENCES AT THREE ANGLES BETWEEN ACTUAL & PREDICTED COLOR VALUES.

FIGURE 9

COMPUTER-IMPLEMENTED NEURAL NETWORK COLOR MATCHING FORMULATION SYSTEM

BACKGROUND OF THE INVENTION

1. Field of the Invention

The present invention relates generally to color matching formulation, and more particularly to artificial neural networks used in color matching formulation.

2. Description of Related Art.

Vehicle paint laboratories perform paint color matching for numerous applications such as painting parts to match other painted parts and surfaces and painting portions of a vehicle that require body repair. Vehicle paint laboratories handle a great deal of complex information such as color measurement data and historical paint formulations. Numerous decisions are also made in color matching based on human analysis of color-related data. A large group of people, equipment and materials are needed to accomplish this task.

Presently, one color matching approach includes identifying the effect pigments with the aid of a microscope and measuring the color values of the standard. Effect pigments include compositions which influence the chromatic and reflective characteristics of the paint. Most notably, effect pigments lend a sparkle characteristic to the paint and may produce color travel. The term "color travel" denotes a color which changes with viewing angle.

Software is used to search databases of previous matches based on the data collected. In some cases, an existing formula may provide a close match. In other instances, the existing match can be utilized as a starting point for the color matching process. In such cases, software may provide a recommendation of correcting this formula. The corrected formula is mixed, sprayed, and compared to the standard. Further formula corrections are performed until the match is deemed suitably close. In some cases, the standard color is so unique that no existing match will serve as a suitable starting point. In these cases, the colors are "matched from scratch." Software is used to produce a best theoretical match of reflectance curves or other color attributes based on pigments selected by a color technician.

A deficiency in this lab process is the color matching correction process. Corrections are performed both with and without the aid of software. In general, too many corrections are performed, and they are often ineffective. Deciding how to correct a formula to better match a color standard is often the most difficult part of color matching. The manner in which the pigments interact with the light and one another to produce the color of the paint is complex. Often more than ten formula correction steps are needed to suitably match metallic or pearl colors. Years of training are required for a technician to learn the subtleties of these interactions and to become proficient at correcting formulas.

Traditional computer software that assists the technician in his tasks has several disadvantages. Traditional computer software has not proven to be very effective on colors containing "effect pigments." This software is typically based on a physical model of the interaction between illuminating light and the coating. These physical models involve complex physics and typically do not account for all aspects of the phenomena. A traditional approach is to use a model based on the work of Kubleka-Munk or modifications thereof The model is difficult to employ with data obtained from multi-angle color measuring devices. One particular difficulty is handling specular reflection that occurs near the gloss angle. Another deficiency of the Kubleka-Munk based models is that only binary or ternary pigment mixtures are used to obtain the constants of the model. The model therefore may not properly account for the complexities of the multiple interactions prevalent in most paint recipes. The present invention overcomes these and other disadvantages. One particular advantage of this invention is that it allows for continual improvement. As new formulation and color measurement sets are created, they can be added to training sets for the neural networks. As the matching processes continue, the performance of the matching system can increase.

SUMMARY OF THE INVENTION

In accordance with the teachings of the present invention, a method and apparatus for color matching are provided that employ paint recipe neural networks. The color of a standard is expressed as color values. The neural network includes an input layer having nodes for receiving input data related to paint recipes. Weighted connections connect to the nodes of the input layer and have coefficients for weighting the input data. An output layer having nodes are either directly or indirectly connected to the weighted connections. The output layer generates output data that is related to the color attributes. The data of the input layer and the data from the output layer are interrelated through the neural network's nonlinear relationship.

Additional advantages and aspects of the present invention will become apparent from the subsequent description and the appended claims, taken in conjunction with the accompanying drawings in which:

DETAILED DESCRIPTION OF THE PREFERRED EMBODIMENTS

Figure 1:
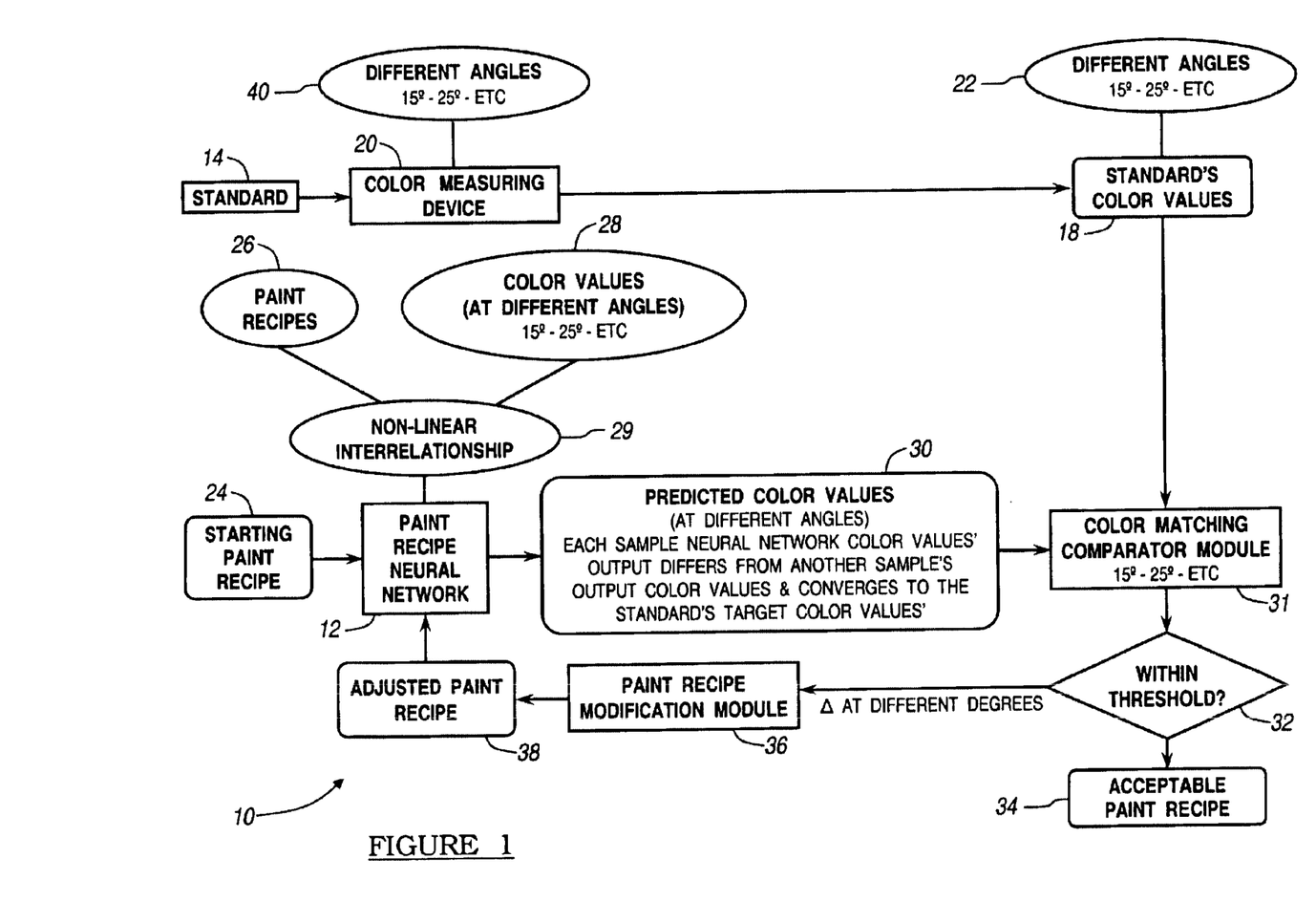
FIG. 1 is a block diagram depicting the components of an alternate embodiment of the present invention's paint recipe neural network.

FIG. 1 shows a paint color matching neural network system generally depicted at 10. A paint recipe neural network 12 performs color matching by determining a paint formula or recipe that substantially matches color values of a standard 14. Color values 18 of a standard 14 are measured by a color measuring device 20. Color values refer to color attributes used to quantify color. Examples include, but are not limited to, reflectance values, tristimulus values and color space values. One example of the latter is L*a*b* color space developed by the Commission International de l'Eclairage. In this system, "L*" represents a luminous intensity. "a*" represents a red/green appearance. "b*" represents a yellow/blue appearance. L*, a* and b* values at various angles are obtained via measurement with a multi-angle color measuring device. From a reflection at a pre-selected angle, the color measuring device 20 determines color values of the standard 14. Thus color values are determined for each pre-selected angle as shown by the reference numeral 22. This color values may include a value designed to quantify color travel. This color value may be a specific combination of the other color values. The color value for quantifying color travel is calculated as the scaled difference between the lightness measured near the gloss angle and at a flop angle.

The color measuring device 20 may determine the color values by illuminating the sample at a specific angle and measuring the reflectance at other angles. One preferred illumination angle is 45 degrees and the preferred observation angles are 25, 45, 75 and 110 degrees measured from the gloss angle. A non-limiting example of the color measuring device 20 is the XRite® Model MA58. Alternatively, a spherical geometry color measuring device typically used with solid color may be used or a digital camera.

The paint recipe neural network 12 of the present invention uses the standard's color values 18 to determine a paint recipe that matches the color of standard 14. A starting paint recipe 24 is provided as input to the paint recipe neural network 12. The starting paint recipe 24 includes different paint compositions or bases, such as a black paint base, a white paint base, a blue paint base, and a red paint base. The starting paint recipe may be provided in a variety of ways, such as searching a database of historic color match formulations. Alternatively, a technician based on his experience or through the use of a formulation guideline may provide the starting paint recipe. In the preferred embodiment, a separate neural network provides the starting paint recipe 24.

It should be understood that the present invention includes using many paint bases that are suitable for the color matching application at hand. For example, if a color of the standard 14 is predominantly a blue color, then the starting paint recipe 24 includes one or more blue paint bases, white and black, and possibly various effect pigments.

The paint recipe neural network 12 examines the starting paint recipe 24 relative to the color values 18 of the standard 14 via its neural network structure that is specially trained to evaluate the non-linear interrelationship 29 between the paint recipes 26 and the color values 28. In one embodiment of the present invention, the paint recipe neural network 12 predicts the color values of a particular paint recipe at angles that correspond to the different angles of the color measuring device 20.

Color matching comparator module 31 compares predicted color values 30 at different angles from the paint recipe neural network 12 to the color values 18 of the standard 14 at corresponding angles to determine how different the predicted color values 30 are from the color values 18 of the standard 14. Color matching comparator module 31 may utilize fuzzy logic to determine the significance of the difference between the predicted color values and color values of the standard 14. Decision block 32 evaluates whether the difference is within a preselected threshold. If the difference is within the preselected threshold, then an acceptable paint recipe 34 is provided as output so that it can be used to formulate paint to match the color of the standard.

If the difference is not within the preselected threshold as determined by the decision block 32, then the current paint recipe is modified by a paint recipe modification module 36. An adjusted paint recipe 38 is provided to the paint recipe neural network 12 so that the new predicted color values 30 can be determined by the paint recipe neural network 12. The new predicted color values 30 are again compared with the standard's color values. The paint recipe is adjusted until the difference is within the preselected threshold. With each iteration, the present invention generates predicted color values that converge to the color value 18 of the standard 14. Paint recipe modification module 36 may apply constraints to the modification process. These may be implemented via fuzzy logic techniques. Constraints are used to enhance the performance of the color matching system or to enforce rules of paint recipe formulation. Enforcement of rules, for example, may include specifications on the minimum and maximum usage amounts for a particular base.

In a preferred embodiment, the paint recipe neural network 12 is a "modular network" with separate networks. The "modular network" provides a group of neural networks, each trained for particular regions of the color space. For example, a separate neural network is used for reds, blues, greens and yellows. Alternatively, a separate neural network can be established for light reds, dark reds, light blues, dark blues, etc.

Paint recipe neural network 12 is used for color formulation correction, matching from scratch, searching databases for the closest match, identification of formula or measurement mistakes in databases, and enhancing paint formula conversion routines. Skilled artisans will appreciate that there are other uses of the paint recipe neural network 12.

Figure 2:
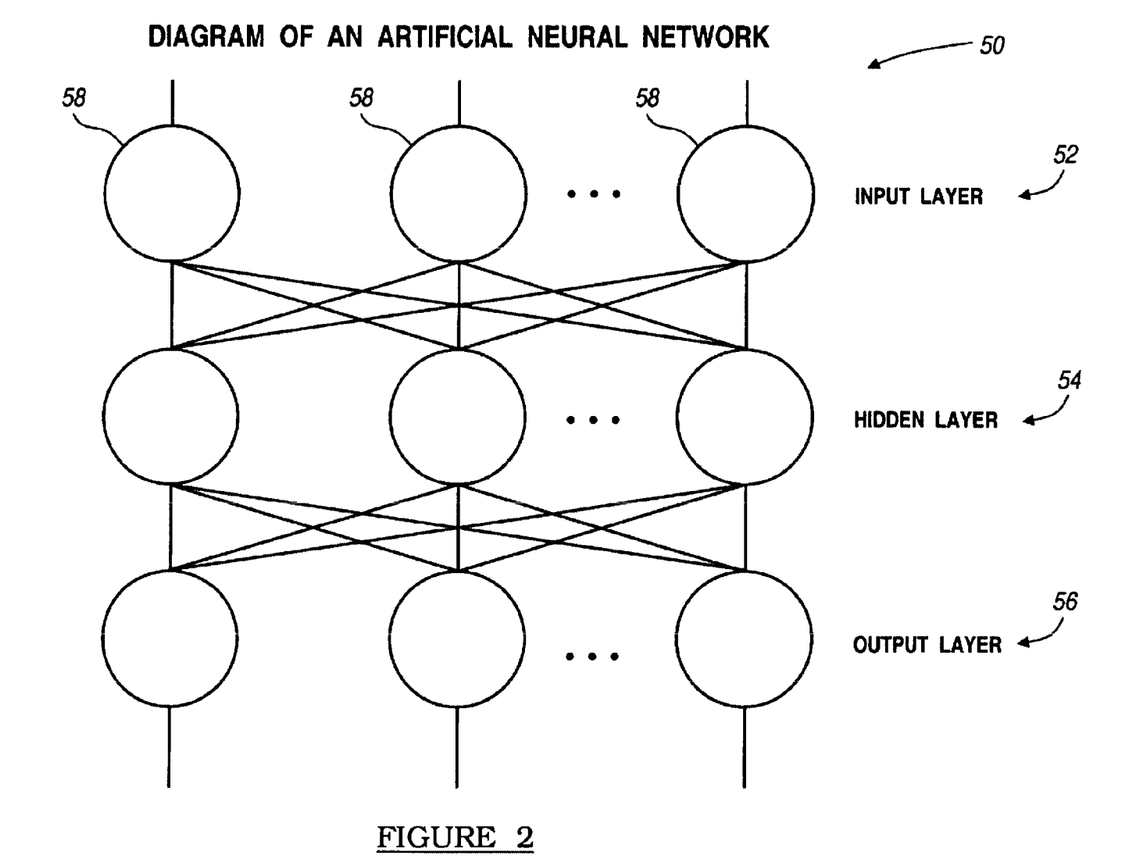
FIG. 2 is a neural network diagram depicting a structure of the paint recipe neural network.

FIG. 2 depicts a neural network 50 diagram used in the paint color matching neural network system. Paint recipe neural network 50 includes three layers of neurons that include an input layer 52, a hidden layer 54 and an output layer 56. The input layer 52 preferably has a number of nodes 58 equal to the number of base paints of a region of the color space used by the modular network approach of the present invention. The hidden layer 54 preferably has a number of neurons equal to the number of input neurons. The output layer 56 represents the color values. For example, in the embodiment that uses L*, a*, b* color values, the output layer contains three neurons representing L*, a*, and b* values for each angle of color measurement for each angle at which color is measured.

Figure 3:
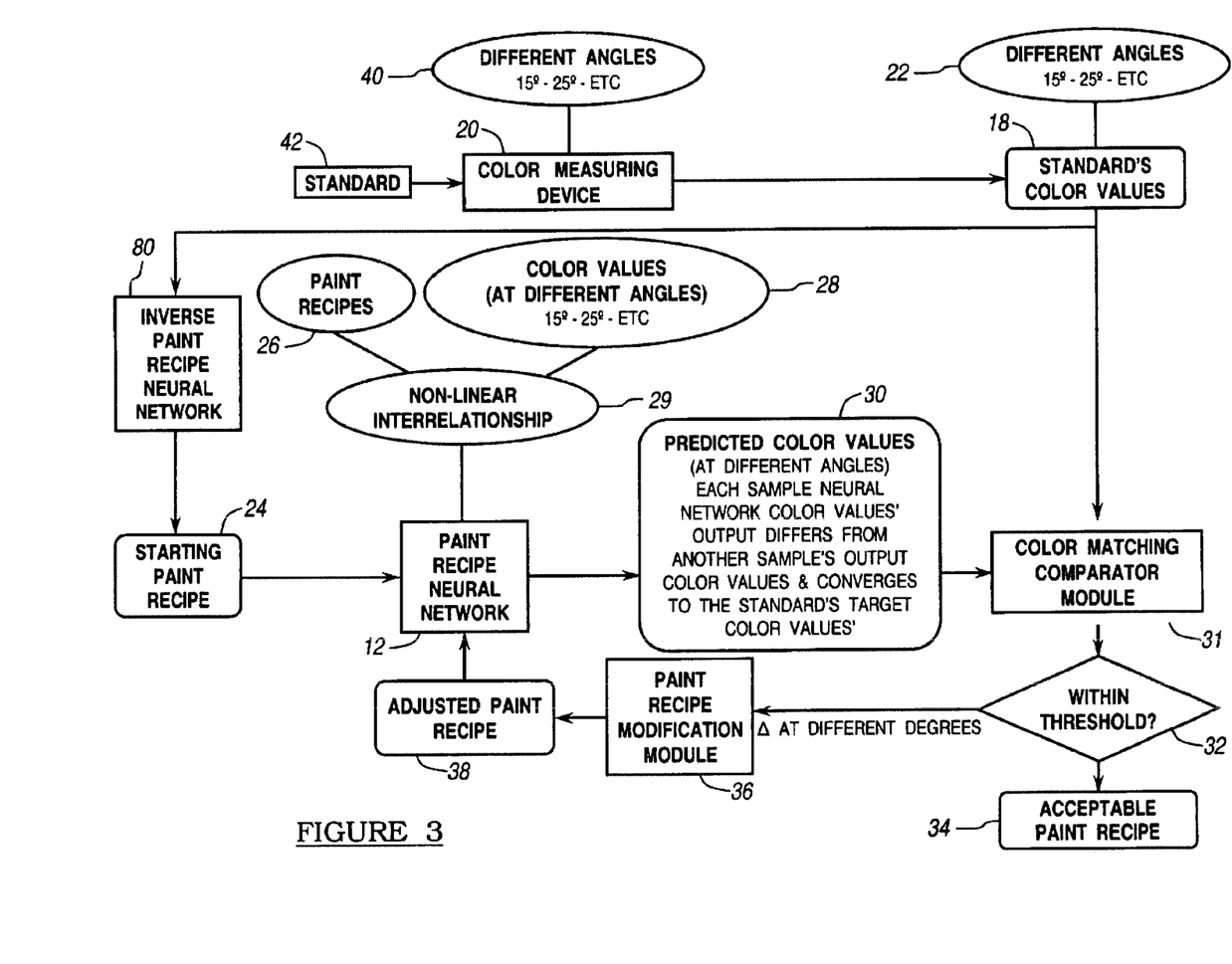
FIG. 3 is a block diagram depicting the components of an alternate embodiment of the present invention that includes an inverse paint recipe neural network.

FIG. 3 depicts an alternate embodiment of the present invention wherein an inverse paint recipe neural network 80 is used to generate the starting paint recipe 24. The inverse paint recipe neural network 80 determines a paint recipe based upon input color values. The inverse paint recipe neural network 80 uses an inverted neural network structure to determine the starting paint recipe 24 in that its input nodes correspond to the input color values (e.g., L*, a*, b*) and its output nodes correspond to paint bases.

Figure 4:
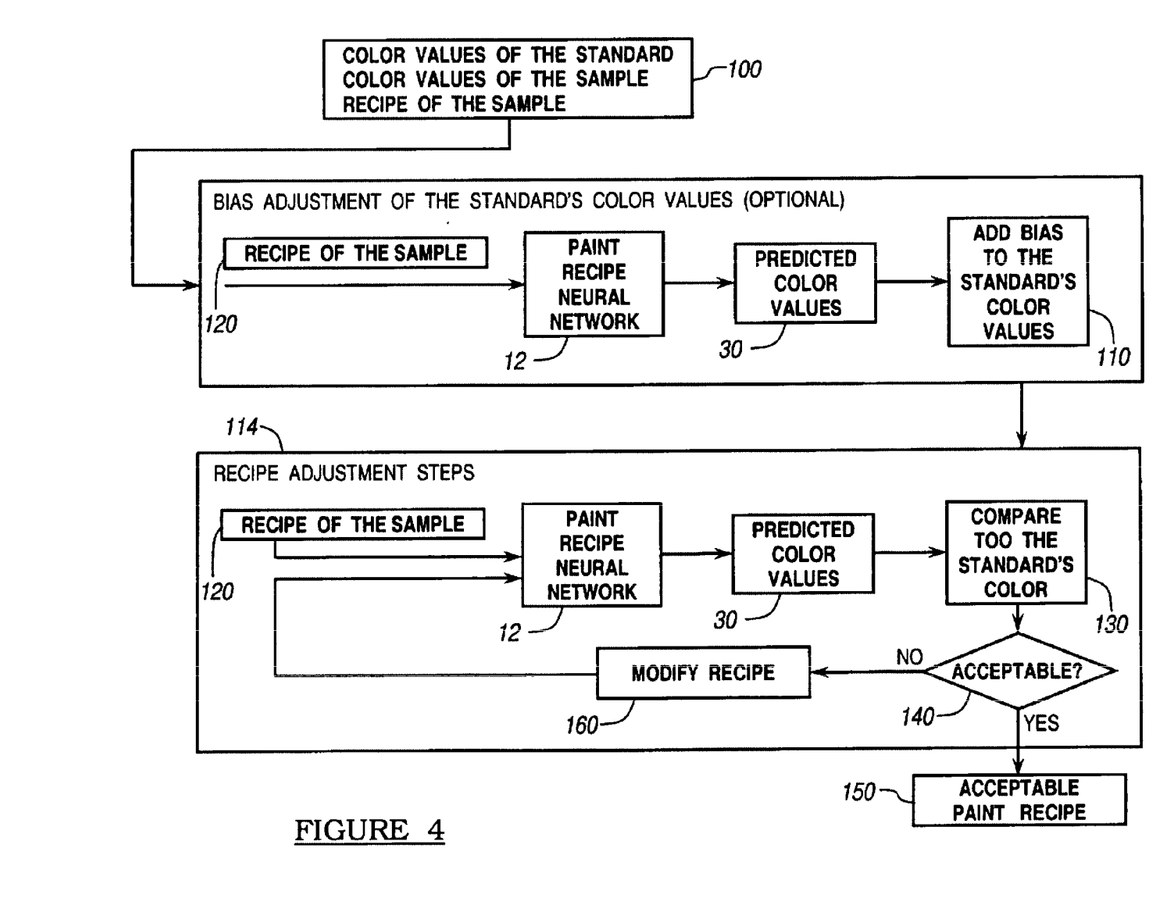
FIG. 4 is a block diagram depicting the components of a first preferred embodiment of the present invention that includes a bias adjustment.

FIG. 4 depicts a preferred embodiment of the present invention wherein the paint recipe neural network 12 is used in a bias adjustment of the color values 18 of the standard 14 prior to recipe correction. The paint recipe neural network 12 generates the predicted color values 30 of the starting recipe based on color matching inputs 100. The predicted color values 30 are used to add bias 110 to the standard's color values. After the bias is added, the recipe adjustment step 114 is performed wherein the paint recipe neural network 12 generates predicted color values 30 based upon the paint recipe 120 of the sample. The adding of bias to the standard's color values is used by the present invention to account for some of the variability present in the color matching processes. The bias compensates for such problems as instrumentation drift, minor variation in base color quality and imperfect fit of the neural network to the data set. The adding of bias to the standard's color values thereby enhances the performance of the paint color matching neural network system. The predicted color values 30 are then compared to the standard's color values at 130. A decision block 140 determines whether an acceptable paint recipe is provided. If an acceptable paint recipe is provided as determined at 150, then the process ends; otherwise, recipe modification occurs at 160 and recipe adjustment 114 iterates.

Figure 5A:
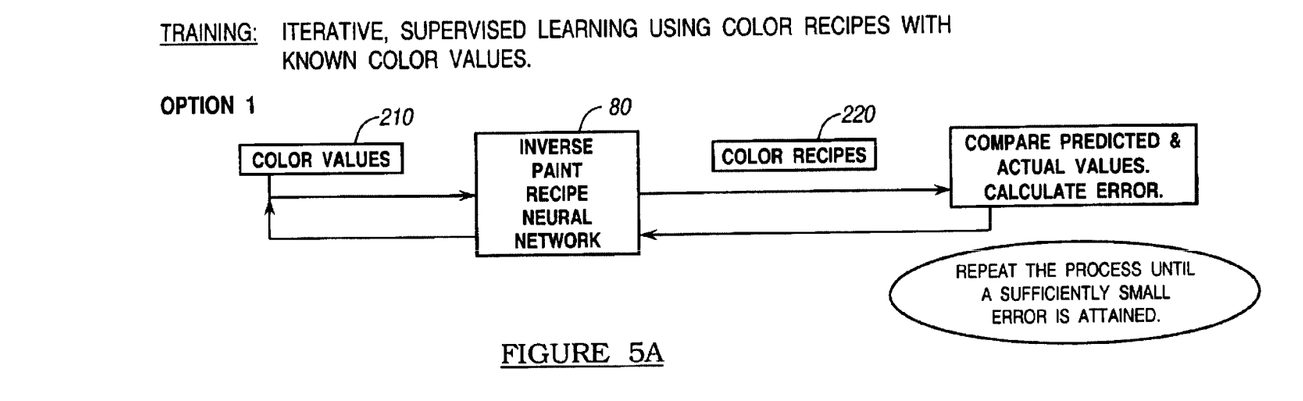
FIGS. 5a and 5b are flow charts depicting training of the present invention paint color matching neural network.
Figure 5B:
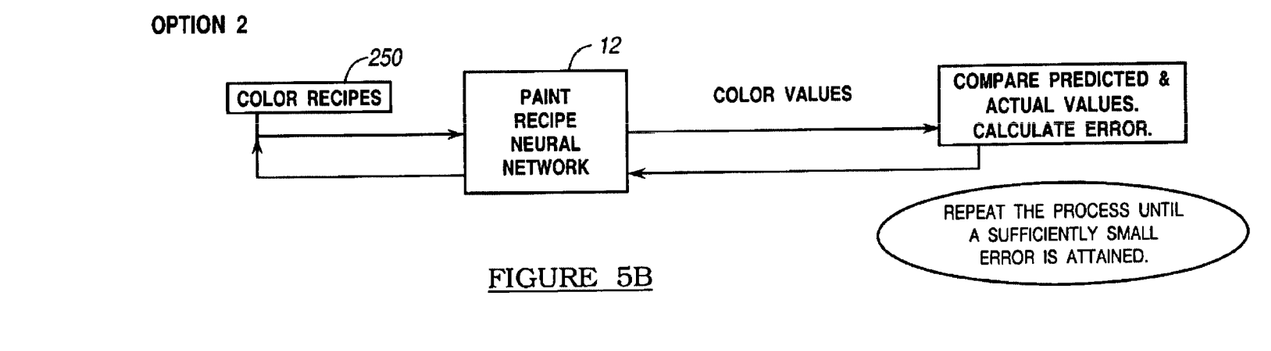

FIGS. 5a and 5b are flow charts depicting training for the paint recipe neural networks. The paint recipe neural networks are trained using the back-propagation training method, although it should be appreciated that other types of training mechanisms could be used. Thousands of epochs (iterations through the training set) were performed for each network. The neural network systems were incorporated into a software program that performs a color correction routine using the relationship between paint recipes and color values learned by the networks. Both the training routines and the color correction program were written in the Java computer language.

With reference to FIG. 5a, the training of the neural network is accomplished by feeding into inverse paint recipe neural network 80 the color values 210 associated with network historic color recipes. Network historic color recipes are developed via the color matching process. The connection weights in the inverse paint recipe neural network 80 are modified until the difference between the predicted and actual recipe is sufficiently small. The adjustment of the weights of the inverse paint recipe neural network 80 is based on the difference.

With reference to FIG. 5b, the training of paint recipe neural network 12 is accomplished by providing the network historic color recipes. The output of the paint recipe neural network 12 is the color values. The connection weights in paint recipe neural network 12 are modified until the difference between the predicted and measured (actual) color values is sufficiently small.

Figure 6:
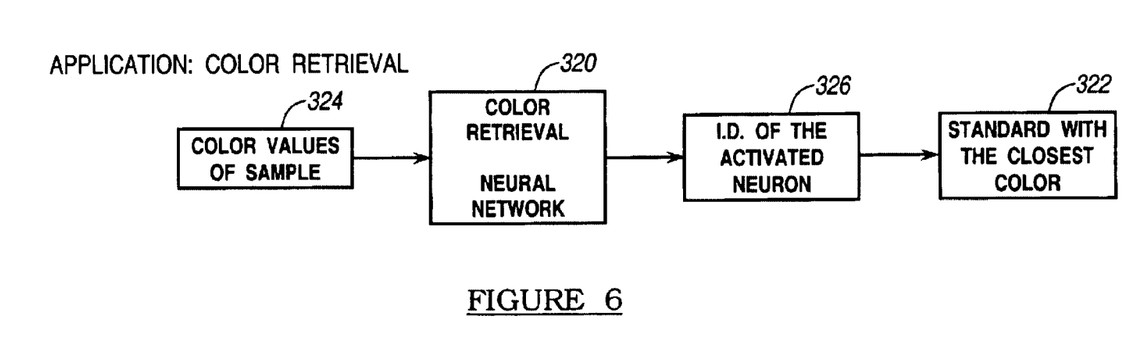
FIG. 6 is a flow chart depicting the use of the paint color matching neural network for a color retrieval application.

FIG. 6 depicts a color retrieval neural network 320. Color retrieval neural network 320 selects a standard 322 that has the closest color to the color values of the sample 324. An advantage to using color retrieval neural network 320 is that through the training process, the color retrieval neural network 320 analyzes the color values for the significant features which distinguish the best retrieval. For example, if the reflectance values are provided as input, color retrieval neural network 320 learns to distinguish the important characteristics of the associated reflectance curves. This analysis ability is learned by color retrieval neural network 320 and does not have to be specifically programmed into the system.

One preferred network architecture is a self-organizing map network. A self-organizing map network uses "internal training" based on competitive learning. A self-organizing map network has one input layer and only one processing layer. Each neuron in the processing layer is connected to the other neurons in this layer. The network has no output layer. For each input vector, a neuron in the processing layer is selected as the best match. The mapping then is from input space to the set of neurons in the processing layer.

For example, if the search database had 1000 members, then the network has 31 inputs (points on the reflectance curve), and contains 1000 neurons in the processing layer, and is trained on the data set. Afterwards, sample data is submitted to the network and the neuron 326 corresponding to the best match member of the search database is selected. The network learns to identify which features of the reflectance curve are important for classifying the colors.

If a database becomes larger, a "modular network" composed of smaller self-organizing map networks can be utilized. This approach simplifies the training process and produces better results. One non-limiting example includes the color space of the search database being split into four parts. A neural network is established for each color space. A fifth network serves as the "conductor" sending the input data to the appropriate network based on L*, a*, b* or reflectance data.

Figure 7:
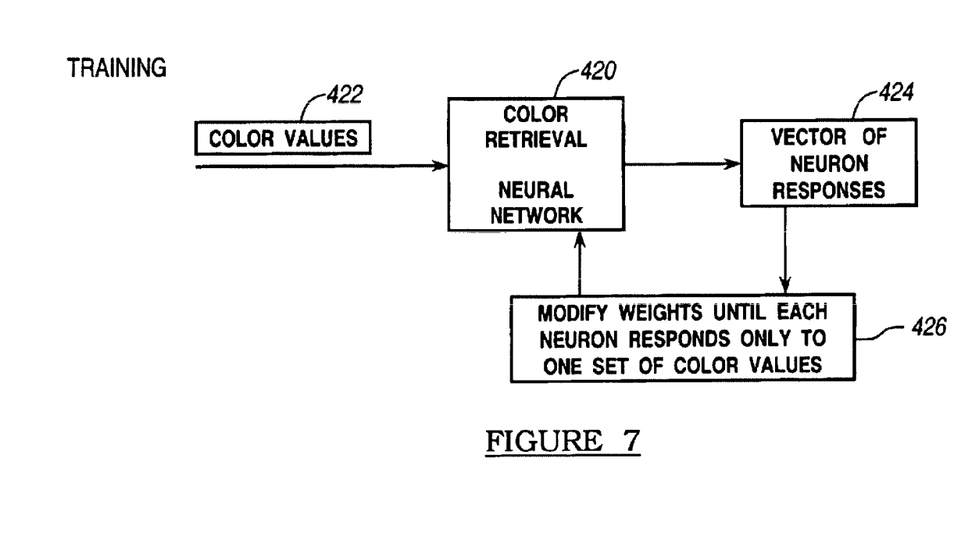
FIG. 7 is a flow chart depicting training of the paint color matching neural network for a color retrieval application.

FIG. 7 depicts the training of the color retrieval neural network 420. Color values 422 of samples are inputted into the color retrieval neural network 420 and a vector of neuron responses 424 is generated. The vector of neuron responses 424 is compared with the desired response. The comparison yields a difference which is used at block 426 to modify the weights until each neuron responds only to one set of color values. If the network architecture is a self-organizing map network, then the self-organizing map network uses "internal training" based on competitive learning.

Figure 8:
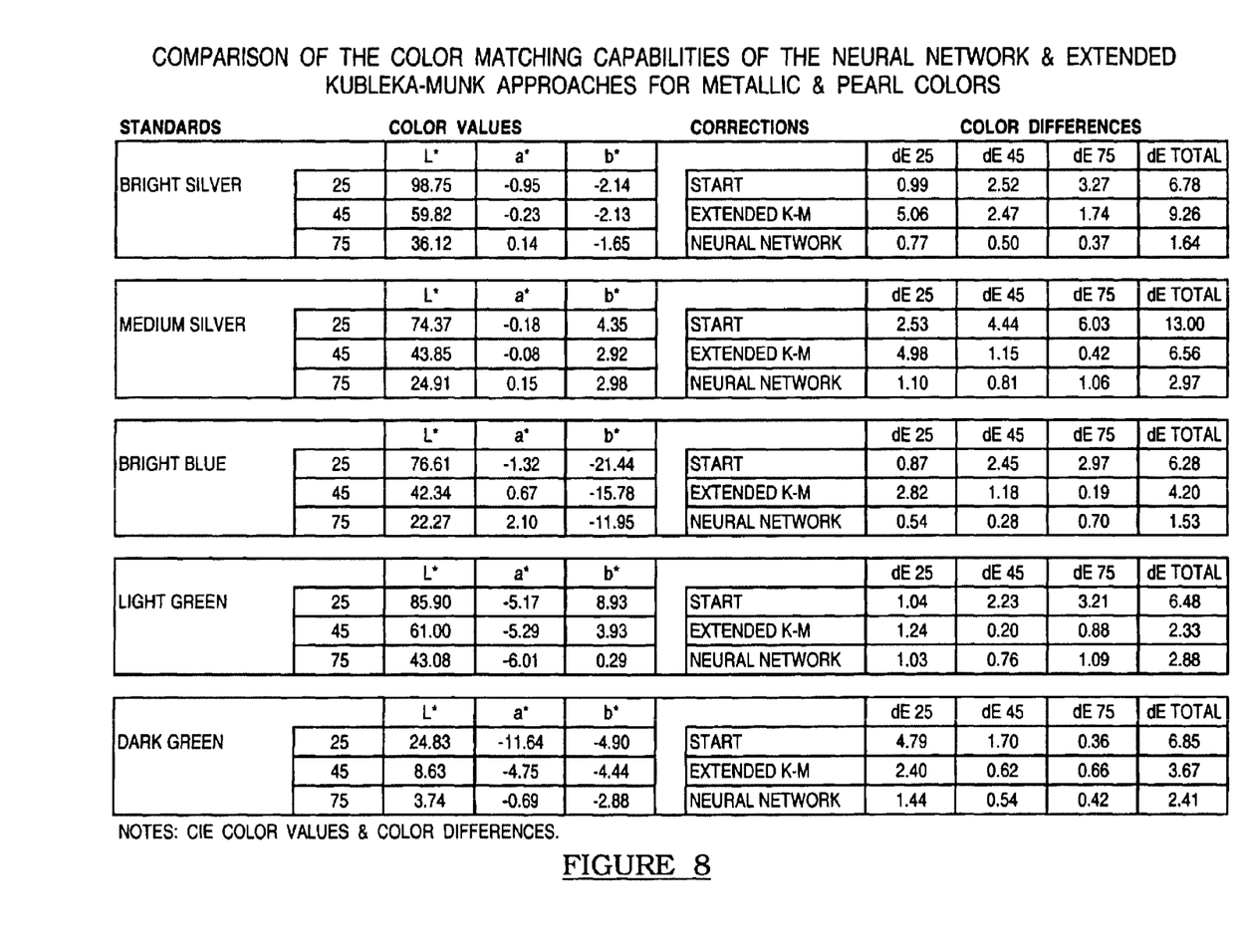
FIG. 8 is a data table depicting a comparison of the color matching capabilities of the neural network and extended Kubleka-Munk approach for metallic and pearl colors.

FIG. 8 depicts the "delta E" results of the color matching neural networks. Within the present invention, the term "delta E" is indicative of the difference between the target color value and another color value. Within the L*, a*, b* color value system, for example, the tem "delta E" represents the Euclidean distance between two sets of L*, a*, b* values. As demonstrated by FIG. 8, the CIE color value differences represented as dE25 (color value differences at 25 degrees), dE45 (color value differences at 45 degrees) and dE75 (color value differences at 75 degrees) between the target and the recipes (predicted by the present invention and sprayed out) decrease for the neural network as compared to the Kubleka-Munk approach.

Figure 9:
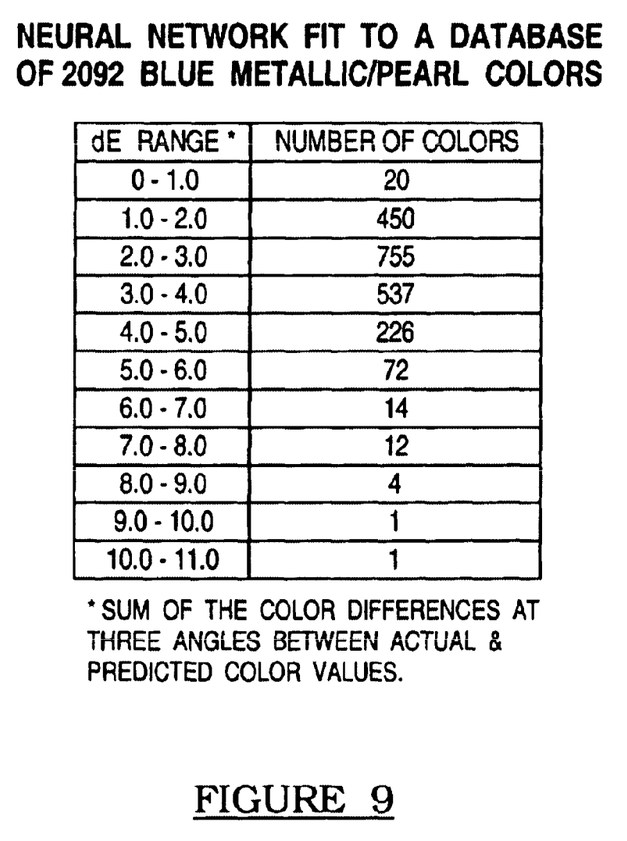
FIG. 9 is a data table depicting the present invention's exemplary training results of blue colors.

FIG. 9 shows the results of the training a paint recipe neural network with blue colors. The "delta E" represents the color difference between the standard's L*, a*, b* color values and network predicted L*, a*, b* color values. These color difference values were sorted into ranges of 1 unit. The "number of colors" associated with each color difference value is provided. For example, there were 755 colors where the difference between predicted and measured color values was between 2.0 and 3.0 dE units, indicating the prediction capability of the paint color matching neural network for a particular training set from the blue color region.

Those skilled in the art can now appreciate from the foregoing description that the broad teachings of the present invention can be implemented in a variety of forms. For example, the color matching neural networks of the present invention handles many different types of color values. Color values that are in cylindrical, spherical coordinates or any color value system derived from reflectance data may be used by the present invention for color matching. Alternatively, the reflectance data may be used. Also, the color matching neural networks of the present invention are applicable to color matching for a variety of paints, such as solid colors and metallic/pearl colors.

Still further, the present invention handles color values derived from many different illuminants at many different angles (especially at the aforementioned "lower" angles). For example, color values at different angles can be measured using incandescent illumination and other types of illuminants (such as, fluorescent lighting). The color matching neural networks of the present invention can produce for a color matching application a paint recipe based upon color values from different illuminants at different angles. The use of different illuminants reduces the problem of metamerism in color matching.

Therefore, while this invention has been described in connection with particular examples thereof, the true scope of the invention should not be so limited since other modifications will become apparent to the skilled practitioner upon a study of the drawings, specification, and following claims.

What is claimed is:

1. A paint color matching system for matching a color standard using paint base colors, comprising:
   an input device for entering an initial paint recipe for said color standard that includes one or more paint bases each having a weight;
   a neural network that includes an input layer that having a plurality of input nodes that are associated with said paint bases, an output layer having a plurality of output nodes representing output color attribute components, and first weighted connections between said input nodes of said input layer with said output nodes of said output layer,
   wherein said first weighted connections determine the contribution of said paint bases at said input layer to each of said output color attribute components; and
   a color comparator for comparing input color attribute components associated with said color standard with said output color attribute components.

2. The paint matching system of claim 1 wherein said color attributes are color dimension components.

3. The paint matching system of claim 1 wherein said plurality of output nodes are first, second and third output nodes that represent first, second and third output color dimension components.

4. The paint color matching system of claim 1 further comprising a color measuring device that generates input color data from said color standard at a plurality of different angles, wherein said input color data includes a plurality of input color dimension components.

5. The paint color matching system of claim 4 wherein said plurality of input color dimension components are first, second and third input color dimension components.

6. The paint color matching system of claim 1 wherein output color dimension components are at a plurality of different angles.

7. The paint color matching system of claim 1 further comprising:
   at least one hidden layer having nodes connected to said first weighted connections, said hidden layer being disposed between said input and output layers; and
   second weighted connections connected to said hidden layer nodes and to said output layer nodes, each of said second weighted connections having a coefficient for weighting said outputs of said hidden layer nodes.

8. The paint color matching system of claim 1 wherein the color values are at angles selected from the group of 15 degrees, 20 degrees, 25 degrees, 45 degrees, 75 degrees, 110 degrees, and combinations thereof.

9. The paint color matching system of claim 1 wherein the color attributes are color values at a flop angle.

10. The paint color matching system of claim 1 wherein the input color attributes and the output color attributes are at angles of 25 degrees, 45 degrees, and a flop angle.

11. The paint color matching system of claim 1 wherein the color attributes are at angles that are less than 30 degrees.

12. The paint color matching system of claim 2 wherein the color dimension components are from a Cartesian coordinate system.

13. The paint color matching system of claim 1 wherein the first dimension of the color coordinate system is indicative of lightness-darkness color attribute, wherein the second dimension of the color coordinate system is indicative of redness-blueness color attribute, wherein the third dimension of the color coordinate system is indicative of yellowness-greenness color attribute.

14. The paint color matching system of claim 1 wherein the input color attribute components and the output color attribute components are derived from the $L^*$, $a^*$, $b^*$ color coordinate system.

15. The paint color matching system of claim 1 wherein the input color attribute components and the output color attribute components are derived from a cylindrical color coordinate system.

16. The paint color matching system of claim 1 wherein the input color attribute components and the output color attribute components are derived from a spherical color coordinate system.

17. The paint color matching system of claim 1 wherein the input data to the input layer includes percentages of at least two paint bases.

18. The paint color matching system of claim 1 wherein the input color attribute components and output color attribute components are a plurality of reflectance values each associated with a specific wavelength.

19. The paint color matching system of claim 1 further comprising:
   a color matching comparator connected to the output layer, said comparator performing a comparison between the color values of the standard at different angles with the color values from the output layer at different angles, said comparison determining the level that the input data of paint bases matches the color of the standard.

20. The paint color matching system of claim 1 wherein the input data to the input layer includes percentages of at least two paint bases, said percentages of the at least two paint bases being at first percentages, said paint color matching system further comprising:
   a color matching comparator connected to the output layer, said comparator performing a comparison between the color values of the standard at different angles with the color values from the output layer at different angles, said comparison determining the level that the input data of paint bases matches the color of the standard; and
   a paint recipe modifier connected to the color matching comparator, said paint recipe modifier adjusting the percentages of the paint bases from the first percentages to second percentages based upon the comparison by the color matching comparator,
   said second percentages of the paint bases being provided as input to the paint color matching system in order to generate second color value output data.

21. The paint color matching system of claim 1 further comprising:
a starting paint recipe system connected to the input layer, said starting paint recipe neural network determining a starting paint recipe based upon the color values of the standard.

22. A color matching system for matching a color of a standard using paint bases, said color of the standard being expressed as color values in a color coordinate system, comprising:
a color measuring device that generates input color values from said color standard at a plurality of different angles;
a neural network that includes an input layer having a plurality of input nodes that are associated with said color values, an output layer having at least one output node that represents a paint recipe for said color standard that includes one or more paint bases, and first weighted connections between said input nodes of said input layer with said output nodes of said output layer,
wherein said first weighted connections determine the contribution of said input color values at said input layer to each of said paint bases at said plurality of different angles; and
a color comparator for comparing said input color values with output color values related to said paint recipe.

23. The color matching system of claim 22 further comprising:
a paint neural network that includes a paint input layer having a plurality of paint input nodes that are associated with said paint bases, a paint output layer having at least one paint output node that represents paint output color attribute components, and first paint weighted connections between said paint input nodes of said paint input layer with said paint output nodes of said paint output layer, wherein said first paint weighted connections determine a contribution of said paint bases at said paint input layer to each of said output color attribute components.

24. A method for matching color of a standard using paint bases using a paint color matching system, said color of the standard being expressed as color values, said method comprising:
receiving input data related to the paint bases at an input layer having nodes, said input data based on color values that are generated at different angles;
assigning a first weighted connection to each of said nodes of said input layer, each of said first weighted connections having a coefficient for weighting said input data;
generating output data from an output layer related to color values, said output data based on paint bases, said output layer having nodes connected to said first weighted connections; and
whereby said output data is calculated from a non-linear relationship between said input data and said output data.

25. The method of claim 24 further comprises:
providing at least one hidden layer having nodes connected to said first weighted connections, said hidden layer being interposed between said input layer and said output layer; and
assigning second weighted connections to each of said hidden layer nodes, each of said second weighted connections having a coefficient for weighting said outputs of said hidden layer nodes.

26. The method of claim 24 wherein the output data is based on at least one of different angles.

27. The method of claim 26 wherein a color measuring device measures the color values of the standard at different angles.

28. The method of claim 26 wherein the color values are at angles selected from the group consisting of 15 degrees, 20 degrees, 45 degrees, 75 degrees, 110 degrees and a combination thereof.

29. The method of claim 26 wherein the color values are color values at a flop angle.

30. The method of claim 26 wherein the color values are at angles of 25 degrees, 45 degrees, and a flop angle.

31. The method of claim 26 wherein the color values are at angles that are less than 30 degrees.

32. The method of claim 26 wherein the color values are each a dimension of a three-dimensional coordinate system indicative of a color attribute.

33. The method of claim 26 wherein the three-dimensional coordinate system is a Cartesian coordinate system.

34. The method of claim 26 wherein the first dimension of the Cartesian coordinate system is indicative of lightness-darkness color attribute, wherein the second dimension of the Cartesian coordinate system is indicative of redness-blueness color attribute, wherein the third dimension of the Cartesian coordinate system is indicative of yellowness-greenness color attribute.

35. The method of claim 26 wherein the Cartesian coordinate system is an L*, a*, b* color coordinate system.

36. The method of claim 26 wherein the three-dimensional coordinate system is a cylindrical color coordinate system.

37. The method of claim 26 wherein the three-dimensional coordinate system is a spherical color coordinate system.

38. The method of claim 24 wherein the input data to the input layer includes percentages of at least two paint bases.

39. The method of claim 25 wherein the input data to the input layer includes percentages of at least two paint bases, said percentages of the at least two paint bases being at first percentages, said method further comprising:
comparing the color values of the standard at different angles with the color values from the output layer at different angles to determine a comparison indicating the level that the input data of paint bases matches the color of the standard;
adjusting the percentages of the paint bases from the first percentages to second percentages based upon the comparing of the color values; and
providing said second percentages of the paint bases being as input to the system in order to generate second color value output data.

40. The method of claim 24 further comprising:
determining a starting paint recipe based upon the color values of the standard via a starting paint recipe system, said starting paint recipe neural network connected to the input layer.

* * * * *